United States Patent [19]

Kimura et al.

[11] 4,380,506

[45] Apr. 19, 1983

[54] PROCESS FOR PRODUCING PRESERVATIVES

[75] Inventors: Yukichi Kimura, Narashino; Takeshi Kanamori, Chiba, both of Japan

[73] Assignee: Lion Corporation, Tokyo, Japan

[21] Appl. No.: 247,249

[22] Filed: Mar. 25, 1981

[30] Foreign Application Priority Data

Apr. 8, 1980 [JP] Japan .................................. 55-45824

[51] Int. Cl.$^3$ ............................................. C09K 15/34
[52] U.S. Cl. ..................................... 252/398; 426/429; 426/541; 426/542; 426/654; 426/655
[58] Field of Search ................ 252/398; 426/429, 541, 426/542, 654, 655

[56] References Cited

U.S. PATENT DOCUMENTS

| | | | |
|---|---|---|---|
| 2,223,244 | 11/1940 | Bohm et al. | 23/250 |
| 2,523,127 | 9/1950 | Lundberg | 260/398.5 |
| 2,571,948 | 10/1951 | Sair et al. | 99/140 |
| 2,950,975 | 8/1960 | Hervey | 99/163 |
| 3,950,266 | 4/1976 | Chang et al. | 252/398 |
| 4,012,531 | 3/1977 | Viani | 426/431 |
| 4,110,483 | 8/1978 | Bishov | 426/542 |

FOREIGN PATENT DOCUMENTS 49-126578 4/1974 Japan .
55-18435 2/1980 Japan .
2033768 5/1980 United Kingdom .

OTHER PUBLICATIONS

Osol et al., The Dispensatory of the United States of America, 1947, pp. 757-765.
Weissberger, Technique of Organic Chemistry, vol. IV: Distillation, 1951, p. 377.
Hawley, The Condensed Chemical Dictionary, 9th Ed., 1977, pp. 684-685.

*Primary Examiner*—J. L. Barr
*Attorney, Agent, or Firm*—Birch, Stewart, Kolasch & Birch

[57] ABSTRACT

A process for producing a preservative having anti-oxidant and anti-bacterial action comprises steps of: preparing a starting material selected from the group consisting of herb family spices, residues obtained after the recovery of essential oils from herb family spices, oleoresins extracted from herb family spices with a polar solvent, and oleoresins extracted from herb family spices with a non-polar solvent and associated residues; subjecting the starting material to extraction with a solvent mixture of polar and non-polar solvents, the ratio by volume of the polar solvent to the non-polar solvent ranging from 2:98 to 50:50; and recovering an extractive to obtain a preservative by distilling off the solvents from said extractive.

8 Claims, No Drawings

PROCESS FOR PRODUCING PRESERVATIVES

BACKGROUND OF THE INVENTION

This invention relates to a process for producing a preservative having anti-oxidant and anti-bacterial action. The preservative may be suitably added to oily and fatty foods, oil and fat containing foods, other foods, cosmetics, medicines and the like.

Herb family spices are known to be an effective anti-oxidant to oils and fats and oily and fatty foods. Researches have been made on this subject with a number of reports. Because of their own strong flavor, these spices or essential oils thereof may be directly added to foods for anti-oxidant action only to a limited extent within which the taste of the foods is not significantly changed. Furthermore, such spices will probably disproportion flavor balance when incorporated into cosmetics, or give rise to an undesired problem due to their own flavor when formulated into medicines.

It is therefore desired to recover a flavorless anti-oxidant fraction from such spices by removing flavoring components. For example, U.S. Pat. No. 3,950,266 discloses a process of preparing an anti-oxidant substance. According to the teachings of this U.S. Patent, powdered rosemary or sage is subjected to extraction with a low boiling solvent such as ethyl ether, and the solvent is distilled off from the resulting extractive to leave a crude product. The crude porduct is washed several times with cold water and then several times with hot water at 80° C., dissolved in a solvent such as methanol, and then treated with activated carbon before the solvent is distilled off from the solution to obtain a refined product (which still has some flavor). Furthermore, the thus obtained product is dissolved in oil and the solution is steam distilled to remove the flavoring components, obtaining a flavorless anti-oxidant substance.

Another extraction process is disclosed in Japanese Patent Application Laid-Open No. 55-18435 in which rosemary or sage is subjected to extraction with 40-60% alcohol in water, water and activated carbon are added to the extractive, and then the solution is separated into a filtrate and a precipitate by filtration. Anti-oxidant fractions are obtained from the filtrate and the precipitate, respectively.

In addition to such typical processes for the extraction treatment of spices using polar solvents, also known are extraction processes using non-polar solvents or oils.

However, the inventors have carried out experiments and found that the extraction treatment of herb family spices such as rosemary and sage with a polar solvent such as ethanol results in an extractive which is inevitably contaminated with bitter components and hence, is somewhat unfavorable in taste. The use of a non-polar solvent such as n-hexane fails to fully extract an anti-oxidant fraction out of the starting spice, resulting in low yields. An extractive containing a high concentration of anti-oxidant components cannot be obtained by the extraction with oils.

It is also recognized that the herb family spices have anti-bacterial action. Relatively large amounts of spices must be added to provide the necessary anti-bacterial action, but the use of such spices in usual ground form will give rise to undesired problems including too strong flavor as discussed above. It is believed that the anti-bacterial action is generally attributable to essential oils. For example, eugenol is known as an anti-bacterial agent and is recovered from the essential oils of spices such as clove and allspice.

SUMMARY OF THE INVENTION

It is an object of the present invention to provide a process for efficiently and readily producing a preservative having excellent anti-oxidant and anti-bacterial action.

Another object of the present invention is to provide a process for producing a substantially flavorless preservative which may be suitably added to foods, cosmetics, medicines or the like.

The present invention is based on the discovery that these objects can be attained by preparing a starting material selected from the group consisting of herb family spices such as sage, rosemary, marjoram, thyme, oregano, basil and the like, residues obtained after the recovery of essential oils from herb family spices, oleoresins extracted from herb family spices with a polar solvent, and oleoresins extracted from herb family spices with a non-polar solvent and associated residues, and subjecting the starting material to extraction with a solvent mixture of polar and non-polar solvents in a particular mixing ratio. The solvent mixture used herein consists of polar and non-polar solvents in a ratio by volume ranging from 2:98 to 50:50, preferably ranging from 5:95 to 25:75. It has been found that when the starting material is subjected to extraction with this solvent mixture, the resulting precipitate has substantially no anti-oxidant action. The active ingredients (both anti-oxidant and anti-bacterial ingredients) in the starting material are efficiently extracted in the resulting extractive which may be dried into a solid preservative having excellent anti-oxidant and anti-bacterial action.

After the extractive is treated with an adsorbent such as activated carbon and the adsorbent is filtered off, water is added to the solution, allowing the polar solvent to migrate into the water and a precipitate to deposit in the non-polar solvent phase. The non-polar solvent phase including the precipitate is collected and subjected to fractionation into the precipitate and a solution phase, the solvent is distilled off from the solution phase and if desired, a residue resulting from the solvent distillation is poured into water for steam distillation, and the residue of the solvent or steam distillation can be recovered as a preservative. This residue is a highly oil-soluble fraction in the form of paste and has a very high anti-oxidant action. The precipitate separated from the solution phase is dried into a substantially oil-insoluble fraction in the form of powder having excellent anti-bacterial action as well as anti-oxidant action. According to the above-mentioned process, both the highly oil-soluble active fraction and the substantially oil-insoluble active fraction can be efficiently obtained at the same time through a common procedure.

According to a first aspect of the present invention, there is provided a process for producing a preservative comprising preparing a starting material selected from the group consisting of herb family spices, residues obtained after the recovery of essential oils from herb family spices, oleoresins extracted from herb family spices with a polar solvent, and oleoresins extracted from herb family spices with a non-polar solvent and associated residues, subjecting the starting material to extraction with a solvent mixture of polar and non-polar solvents, the ratio by volume of the polar solvent to the non-polar solvent ranging from 2:98 to 50:50, preferably ranging from 5:95 to 25:75, and recovering an extractive as a preservative.

In the practice of the present invention, a solid preservative is obtained by distilling off the solvents from the extractive and optionally effecting steam distillation, and recovering the resulting solid matter.

According to a second aspect of the present invention, there is provided a process for producing a preservative comprising following the steps of the process according to the first aspect, adding an adsorbent to the extractive, adding water to the extractive after the adsorbent is separated, allowing the polar solvent to migrate into the water, separating a water/polar solvent phase from a non-polar solvent phase having a highly oil-soluble active fraction dissolved and a substantially oil-insoluble active fraction precipitated, and recovering the non-polar solvent phase as a preservative. More particularly, a solid preservative is obtained by distilling off the solvent from the non-polar solvent phase and optionally effecting steam distillation, and recovering the resulting solid matter.

According to a third aspect of the present invention, the non-polar solvent phase is separated into a solution having the highly oil-soluble active fraction dissolved and a precipitate containing the substantially oil-insoluble active fraction. The solvent is evaporated off from the solution and optionally steam distillation is effected to collect a pasty mass from the evaporated residue, thereby recovering the oil-soluble active fraction in the form of paste as an anti-oxidant preservative. On the other hand, the precipitate is dried to recover the oil-insoluble active fraction in the form of powder as an anti-bacterial preservative.

As an extractive is obtained by subjecting the starting material to extraction with a solvent mixture of polar and non-polar solvents in a ratio by volume ranging from 2:98 to 50:50, both the highly oil-soluble active fraction and the substantially oil-insoluble active fraction can be efficiently recovered in high yields through a common procedure. The procedure consists of a limited number of simple steps so that the preservative can be efficiently obtained at low cost. Furthermore, the non-polar solvent phase may be readily separated into the highly oil-soluble active fraction and the substantially oil-insoluble active fraction.

Although the residues obtained after distillation or extraction of essential oils or oleoresins from herb family spices have heretofore been discarded as unuseful wastes, the process of the present invention enables to use such residues as the starting material for extraction. Therefore, an additional advantage is obtained that effective use can be made of such residues which are otherwise discarded.

The preservatives obtained in the form of paste, solid or powder according to the present invention contain relatively high concentrations of active ingredients. The preservatives are very easy to handle, substantially free of the flavor inherent to a particular starting spice, and lightly colored particularly when steam distillation and adsorption treatment are effected. The preservatives need not necessarily be added in large amounts to provide a preservative effect. Therefore, the addition of the present preservatives to foods will neither alter the flavor or color of the foods nor give rise to a problem in safety aspect. Accordingly, the present preservatives are very useful in food applications. They will not disproportion flavor balance when incorporated into cosmetics while they may be formulated into medicines without changing the color or odor thereof.

The preservatives obtained by the process of the present invention exhibit excellent anti-oxidant action, and particularly the highly oil-soluble active fraction in the form of paste obtained by separating the non-polar solvent phase into a solution phase and a precipitate and distilling off the solvent from the solution phase according to the third aspect of the present invention exhibits remarkably high anti-oxidant action. When added to lard, for example, this oil-soluble active fraction is effective to prevent oxidation of lard for increased periods of time, exerting at least equal anti-oxidant action as compared with butylhydroxy anisole (BHA) which has hitherto been used as a synthetic anti-oxidant. Furthermore, the substantially oil-insoluble active fraction in the form of powder obtained by drying the precipitate separated from the non-polar solvent phase exhibits somewhat less anti-oxidant action than the abovementioned highly oil-soluble active fraction, but is highly effective in inhibiting bacterium and fungi from propagating. When added to foods, this oil-insoluble active fraction is effective in preventing oxidation and rotting of the foods.

The above and other objects, features and advantages of the present invention will become more apparent and understandable from the following descriptions.

DETAILED DESCRIPTION OF THE INVENTION

The starting materials used in the practice of the present invention are herb family spices including sage, rosemary, marjoram, thyme, oregano, basil and the like. Various modified types of the starting materials may also be used in the practice of the present invention, including powders of these spices; residues obtained after the recovery of essential oils from the spices by steam distillation or similar residues; oleoresins obtained from the extraction of the spices with a polar solvent such as ethyl ether, ethylene chloride, dioxane, acetone, ethanol, hydrous ethanol, methanol, ethyl acetate, propylene glycol, glycerin or the like; and oleoresins and extracted residues obtained from the extraction of the spices with a non-polar solvent such as n-hexane, petroleum ether, ligroin, cyclohexane, carbon tetrachloride, chloroform, dichloromethane, 1,2-dichloroethane, toluene, benzene or the like.

A preservative may be obtained from the starting material by first subjecting it to extraction with a solvent mixture consisting of polar and non-polar solvents in a ratio by volume ranging from 2:98 to 50:50, preferably ranging from 5:95 to 25:75 and recovering an extractive. The extraction with the solvent mixture of polar and non-polar solvents in the above-specified volume ratio allows both the highly oil-soluble active fraction and the substantially oil-insoluble active fraction to fully migrate into the extractive so that the active ingredients may be extracted in high yields. The presence of more than 50% by volume of the polar solvent in the solvent mixture will cause a substantial amount of bitter ingredients to migrate into the extractive, providing the extractive with an undesired taste. On the other hand, if the polar solvent is present in amounts less than 2% by volume, the anti-oxidant ingredients will not be extracted from the starting material or spice in high yields. The object of the present invention is achievable only within the above-specified range of the ratio of polar to non-polar solvents.

Examples of the polar solvent which may be used as one component of the solvent mixture in the practice of the present invention include acetone, ethanol, methanol, propyleneglycol, glycerin and other polar solvents compatible with water, and mixtures thereof. Most preferred among them is ethanol when volatility and viscosity are taken into account for the subsequent procedures, and particularly when the retention of the solvent used is a consideration as in the case of foods. Examples of the non-polar solvents used herein include n-hexane, petroleum ether, ligroin, cyclohexane, carbon tetrachloride, chloroform, dichloromethane, 1,2-dichloroethane, toluene, benzene, and mixtures thereof. Most preferred among these are n-hexane and petroleum ether because of their volatility and safety.

In order to effect extraction, at least an equal volume of the solvent mixture is added to the starting material. Or at least two parts by weight of the solvent mixture are used to one part by weight of the starting material. Extraction may be effected at room temperature with agitation or under reflux for a period of ½ hour to overnight. This mixture is separated into an extractive and a residue in a conventional manner as by filtration, centrifugal separation or decantation, preferably under warming. The resulting residue is preferably again subjected to the same extraction treatment as above to thereby obtain an additional extractive which is combined with the precedent extractive.

The solvents may be distilled off from the combined extractive, and if desired, the resulting solid matter is poured into water for steam distillation. The solid residue of the solvent or steam distillation is recovered as a solid preservative. It is to be noted that this preservative contains both a substantially oil-insoluble active fraction and a highly oil-soluble active fraction in admixture as will become apparent from the following description.

According to the second aspect of the present invention, any suitable adsorbent such as activated carbon, diatomaceous earth, acid clay or the like is added to the extractive to remove coloring matters such as chlorophyll from the extractive for decoloring. The adsorbent is then filtered off to leave a treated solution. Thereafter, water is added to the solution, allowing the polar solvent to migrate from the non-polar solvent to the water. The non-polar solvent phase is then collected. More particularly, in the adsorption step, the adsorbent is added to the extractive in an amount of 1–20% by weight based on the weight of the starting material. After refluxing or stirring at room temperature for 10 to 60 minutes, the adsorbent is filtered off to leave a treated solution. This adsorption step is usually carried out once or twice. The thus obtained solution exhibits light or dark brown due to the removal of green coloring matters and the like. A 0.3 to 3-fold volume of water is added to the solution, thoroughly mixed therewith, and then allowed to stand. As a result, the polar solvent which has been in the solution migrates into the water and thus the mixture separates into a water/polar solvent phase and a non-polar solvent phase, with a highly oil-soluble active fraction being dissolved in the non-polar solvent phase and a substantially oil-insoluble active fraction being precipitated in the same phase. Since both the active fractions are thus present in the non-polar solvent phase, an active composition (containing both the active fractions) may be efficiently recovered simply by collecting the non-polar solvent phase.

After being separated from the water/polar solvent phase, the non-polar solvent phase may be subjected to distillation to remove the non-polar solvent, thereby collecting a solid matter containing the highly oil-soluble active fraction and the substantially oil-insoluble active fraction in admixture, which is easy for use as a solid preservative.

The respective fractions may be separately obtained when separate preservative may more advantageously be applied because of their quality difference as exemplified by a difference of solubility in oils. To this purpose, the above-mentioned non-polar solvent phase is separated into a solution and a precipitate by filtration, centrifugal separation, decantation, or the like. The solvent is distilled off from the solution and optionally steam distillation is effected to recover the highly oil-soluble active fraction in the form of paste while the precipitate is dried to recover the substantially oil-insoluble active fraction in the form of powder.

The steam distillation which may optionally be effected to recover the highly oil-soluble active fraction may be carried out in the same manner as the steam distillation which may optionally be effected after the solvents are distilled off from the initial extractive based on the solvent mixture. More particularly, a solid residue obtained by distilling off the solvent from the solution is poured into water, preferably in an about ten or more times larger amount than the weight of the solid, and dispersed in the water by agitation. The dispersion is heated under atmospheric or reduced pressure to the boiling point of water. By this steam distillation, essential oils exhibiting the flavor inherent to the starting spice are removed from the aqueous dispersion as they volatilize away together with steam. The steam distillation therefore minimizes the flavor and color of the highly oil-soluble active fraction or an end fraction. It will be understood that steam may be blown into the aqueous dispersion during this steam distillation to promote the volatilization of essential oils. The steam distillation is continued until substantially no trace of essential oils is detected in a sample of the distillate. The remaining aqueous dispersion, optionally after cooling, is separated into an aqueous phase and a pasty mass in a conventional manner as by filtration, centrifugal separation and decantation. The thus collected mass is used as a preservative.

The thus obtained preservatives including the pasty fraction (the highly oil-soluble active paste), the powdery fraction (the substantially oil-insoluble active powder) or the mixtures thereof are more or less free of the flavor inherent to the starting spice and have remarkable anti-oxidant action. They may be added to a variety of products including oily and fatty foods, for example, fats such as lad, tallow, chicken oil and fish oils, oils such as soybean oil, linseed oil, cottonseed oil, safflower oil, rice-bran oil, corn oil, coconut oil, palm oil, sesame oil, cacao butter, castor oil, peanut oil, etc.; oil and fat containing foods such as butter, cheese, margarine, shortening, mayonnaise, dressing, ham, sausage, potato chips, fried crackers, fried noodles, compacted curry roux, etc.; other foods, for example, soy sauce, juice, refregerants, alcohol beverages, fruit wine, ketchup, jam, processed marine and livestock products, etc.; cosmetics, for example, hair and skin lotions and tonics, lip creams, etc.; and medicines. Particularly, because of its outstanding anti-oxidant action and high solubility in edible oils and fats, the pasty fraction may most advantageously be applied to oily and fatty foods and oil and fat containing foods as an anti-oxidant. On the other hand, as the powdery fraction is somewhat less anti-oxidant than the pasty fraction, but has superior anti-bacterial action, it may preferably be added to processed marine and livestock products, etc. It is preferred to select any suitable one among the pasty fraction, the powdery fraction and the mixture thereof so as to meet the requirement of an intended use.

The preservatives according to the present invention may preferably be added in an amount of 0.00001 to 2% by weight, especially 0.005 to 1% by weight. The preservatives may be added undiluted or diluted with a suitable solvent. The pasty fraction may be dissolved in oils or fats at high concentrations before it is added. The powdery fraction may be dissolved in ethanol, propylene glycol, glycerin or mixtures thereof for better dispersion, handlability. The powdery fraction may also be processed into powder or granule form by adding thereto a vehicle such as starch and gelatin.

In order that those skilled in the art will better understand how to practice the present invention, exmaples are set forth below by way of illustration, but not by way of limitation.

EXAMPLE 1

To 100 g of powdered sage was added 500 ml of each of the solvents shown in Table 1. Each mixture was allowed to stand for about one hour for extraction before it was separated into an extractive and an insoluble by filtration. The insoluble was washed with a fresh solvent of the same type as used for the extraction and the resulting liquid was combined with the extractive. The solvent was distilled off from the combined extractive to leave a solid matter. The yields of the solid matters are shown in Table 1.

Each of the solid matters obtained above was added to lard in an amount of 0.02% by weight and the lard was tested for oxidation resistance according to the Active Oxygen Method (AOM) as mentioned below.

A 20-g portion of purified lard containing 0.02% by weight of each solid matter obtained above was weighed in a test tube which was placed in a constant temperature oil bath at 97.5° C.±0.5° C. Air was forcibly introduced into the lard at a rate of 0.23 ml per hour. A sample was taken out of the lard at suitable intervals and determined for peroxide value (POV) according to the modified version of Lea method. The results are expressed in terms of an aeration stability time (hour) which had passed until the POV reached 30 meq/kg.

Pure lard containing no solid matter had an aeration stability time of 8.0 hours.

Further, corn salad oil containing 0.1% by weight of each solid matter obtained above was evaluated for taste using ten sensory testing panels.

Evaluation criterion
- −: substantially no bitterness
- ±: a low, but allowable degree of bitterness
- +: bitter
- ++: extremely bitter In an additional test, each of the above-obtained solid matters was added to soybean salad oil at a concentration of 20% by weight. The oil was visually observed to determine the solubility of each solid matter in oil.

The results of the aeration stability, sensory and solubility tests are shown in Table 1.

TABLE 1

| Solvent system* | Yield (%) | Aeration stability (hour) | Taste | Solubility in oil | Anti-oxidation value** | Remarks |
|---|---|---|---|---|---|---|
| ethanol | 21.3 | 20.0 | ++ | deposit | 426 | Comparison |
| n-hexane | 6.1 | 52.5 | − | uniform dispersion | 320 | Comparison |
| petroleum ether | 5.9 | 51.0 | − | uniform dispersion | 300 | Comparison |
| ethyl ether | 10.5 | 38.5 | + | slight deposit | 385 | Comparison |
| acetone | 19.5 | 21.0 | ++ | deposit | 410 | Comparison |
| ethanol/n-hexane (2/98) | 6.8 | 55.9 | − | slight deposit | 380 | Invention |
| ethanol/n-hexane (5/95) | 7.2 | 60.0 | − | slight deposit | 432 | Invention |
| ethanol/n-hexane (10/90) | 8.5 | 50.0 | ± | slight deposit | 425 | Invention |
| ethanol/n-hexane (25/75) | 10.8 | 40.0 | ± | slight deposit | 432 | Invention |
| ethanol/n-hexane (50/50) | 15.2 | 26.0 | + | deposit | 395 | Invention |
| ethanol/n-hexane (75/25) | 17.4 | 23.5 | ++ | deposit | 409 | Comparison |
| ethanol/n-hexane (95/5) | 18.1 | 24.0 | ++ | deposit | 434 | Comparison |

*Parts by volume
**The anti-oxidation value is a value of an yield (percent) multiplied by an aeration stability time (hour). It is a measure for determining the degree of extraction of anti-oxidant contents from the starting material with a particular solvent system. Higher values indicate better anti-oxidant action.

As seen from the results of Table 1, the extraction with solvent mixtures consisting of ethanol (polar solvent) and n-hexane (non-polar solvent) in a relative ratio by volume of 2:98 to 50:50, preferably 5:95 to 25:75 results in fractions improved in both anti-oxidant action and taste.

EXAMPLE 2

To 50 g of powdered rosemary was added 250 ml of a solvent mixture consisting of 10 parts by volume of ethanol and 90 parts by volume of n-hexane. The mixture was refluxed for 1.5 hours before it was filtered into a filtrate and a residue. The residue was further mixed with 250 ml of a fresh solvent mixture of the same composition as above and again subjected to extraction under reflux for 1.5 hours. The mixture was filtered into a filtrate and a residue and this filtrate was combined with the previous one.

To the combined filtrate was added 0.5 g of activated carbon. After stirring for one hour, the mixture was filtered. 360 ml of the filtrate was added to 360 ml of water, thoroughly mixed therewith by agitation, and then allowed to stand. The ethanol migrated into the water and as a result, the mixture separated into a water/ethanol phase and an n-hexane phase having solids precipitated.

This n-hexane phase was collected and separated into a solution and a precipitate by filtration. The n-hexane was distilled off from the solution and the resulting residue was poured into 50 ml of water and subjected to steam distillation for one hour, obtaining 1.94 g of a residue which was a brown pasty fraction designated fraction A. On the other hand, the precipitate was dried to give 2.30 g of a yellowish white powdery fraction designated fraction B.

The above-described procedure was repeated until the n-hexane phase having solids precipitated was obtained. The solvent was distilled off from the n-hexane phase with the precipitate kept therein. The resulting residue was poured into 50 ml of water and subjected to steam distillation for one hour, obtaining 4.26 g of a residue designated fraction C.

Similar fractions A to C were obtained by repeating the above-described procedure except that the powdered rosemary was replaced by 50 g of a dried residue obtained by steam distillating rosemary and no further steam distillation was effected in the subsequent steps.

The respective fractions were subjected to the same aeration stability, sensory and solubility tests as described in Example 1.

Furthermore, the flavor of the respective fractions was evaluated by dispersing or dissolving each fraction in corn salad oil at a concentration of 0.1% by weight. Using ten sensory testing panels, flavor evaluation was made according to the following criterion.
−: flavorless
±: a low, but allowable degree of flavor
+: a moderate degree of flavor
++: extremely strong flavor In addition, 0.01% ethanol solutions were prepared from the respective fractions and determined for anti-bacterial action according to the cylinder plate method.
Measuring conditions
Culture medium: Tripticase soy agar
Fungus: Bacillus subtilis
Cultivating conditions: 30° C., 36 hours
Evaluation criterion
+++: clear inhibitory circle
++: fair inhibitory circle
+: semi-turbid inhibitory circle
±: observable minimum inhibitory circle
−: equal to the blank (system consisting of ethanol)

TABLE 2

| Starting material | Fraction | Yield (%) | Aeration stability (hr.) | Taste | Flavor | Solubility in oil | Antibacterial action |
|---|---|---|---|---|---|---|---|
| Powdered rosemary | A | 3.9 | 50.0 | − | ± | easily soluble | ± |
|  | B | 4.6 | 28.5 | ± | − | substantially insoluble | +++ |
|  | C | 8.5 | 40.0 | ± | ± | turbid | ++ |
| Steam distillation residue of rosemary | A | 4.3 | 49.5 | − | ± | easily soluble | ± |
|  | B | 3.5 | 29.0 | ± | − | substantially insoluble | +++ |
|  | C | 7.9 | 41.0 | ± | ± | turbid | ++ |

As seen from the results of Table 2, fraction B is insoluble in oil, slightly bitter, flavorless and highly anti-bacterial, whereas fraction A is easily soluble in oil, least bitter and highly anti-oxidant, but has little anti-bacterial action.

EXAMPLE 3

Each of powdered marjoram, thyme, oregano and basil (100 g) was subjected to extraction with a single ethanol system, a mixed ethanol/n-hexane (1/9) system and a single n-hexane system. The solvent(s) was distilled off from the resulting extractive to leave a solid matter. In addition, an extracted matter resulting from extraction with ethanol was further subjected to extraction with n-hexane and the solvent (n-hexane) was distilled off from the resulting extractive to leave a solid matter. In either case, the amount of solvent used was 500 ml and extraction was effected at 50° C. for two hours.

A comparison was made among the thus obtained solid matters. Those solid matters obtained using the mixed ethanol/n-hexane system tasted substantially no bitter and formed a trace of deposit when dispersed or dissolved in corn salad oil. Those obtained using the single ethanol system tasted strongly bitter and dissolved sparingly in corn salad oil. Further, those obtained using the mixed ethanol/n-hexane system showed good anti-oxidant action with respect to corn salad oil whereas those obtained using the single n-hexane system and those obtained using the single ethanol sysyem followed by the single n-hexane system failed to fully extract the anti-oxidant fraction from the starting spice powder. These results apply to all the starting spices.

In the cases of using an oleoresin extracted from sage with ethanol, an oleoresin extracted from rosemary with n-hexane and the associated residue as starting materials, the same results were obtained.

What is claimed is:

1. A process for producing a preservative, comprising the steps of:
    preparing a starting material selected from the group consisting of herb family spices, residues obtained after the recovery of essential oils from herb family spices, oleoresins extracted from herb family spices with a polar solvent, and oleoresins extracted from herb family spices with a non-polar solvent and associated residues, said herb family spices being selected from the group consisting of sage, rosemary, majooram, thyme, oregano and basil;
    subjecting the starting material to extraction with a solvent mixture of a polar solvent compatible with water and a non-polar solvent selected from the group consisting of n-hexane, petroleum ether, ligroin, cyclohexane, carbon tetrachloride, chloroform, dichloromethane, 1,2-dichloroethane, toluene, benzene and mixtures thereof, the ratio by volume of the polar solvent to the non-polar solvent ranging from 2:98 to 50:50;
    adding an adsorbent to said extractive in an amount of 1–20% by weight based upon the weight of the starting material;
    adding water to the extractive after said adsorbent is separated;
    allowing the polar solvent to migrate into the water;

separating the mixture into a water/polar solvent phase and a non-polar solvent phase having a highly oil-soluble active fraction dissolved and a substantially oil-insoluble active fraction precipitated; and recovering the non-polar solvent phase as a preservative.

2. A process according to claim 1 wherein the ratio by volume of the polar solvent to the non-polar solvent ranges from 5:95 to 25:75.

3. A process according to claim 1 which further comprises after the non-polar solvent phase having the highly oil-soluble active fraction dissolved and the substantially oil-insoluble active fraction precipitated is collected, separating said non-polar solvent phase into a solution having the highly oil-soluble active fraction dissolved and a precipitate containing the substantially oil-insoluble active fraction, distilling off the solvent from said solution to leave a pasty matter, thereby recovering the oil-soluble active fraction in the form of paste as an anti-oxidant preservative, and drying said precipitate, thereby recovering the oil-insoluble active fraction in the form of powder as an anti-bacterial preservative.

4. A process according to claim 3 wherein steam distillation is effected after said pasty matter is poured into water to recover a residue as an anti-oxidant preservative.

5. A process according to claim 1 which further comprises after said non-polar solvent phase having the highly oil-soluble active fraction dissolved and the substantially oil-insoluble active fraction precipitated is collected, distilling off the solvent from said non-polar solvent phase, thereby recovering a solid matter containing both said active fractions mixed as a preservative.

6. A process according to claim 5 wherein steam distillation is effected after said solid matter is poured into water to recover a residue as a preservative.

7. A process according to claim 1 wherein the starting material is a residue obtained after extraction of essential oils or oleoresins from herb family spices.

8. A process for producing a preservative, comprising the steps of:

preparing a starting material selected from the group consisting of herb family spices having antioxidant values, residues obtained after the recovery of essential oils from herb family spices, oleoresins extracted from herb family spices with a polar solvent, and oleoresins extracted from herb family spices with a non-polar solvent and associated residues;

subjecting the starting material to extraction with a solvent mixture of a polar solvent compatiable with water and a non-polar solvent, the ratio by volume of the polar solvent to the non-polar solvent ranging from 2:98 to 50:50;

adding an effective amount of an adsorbent to said extractive;

adding water to the extractive after said adsorbent is separated;

allowing the polar solvent to migrate into the water;

separating the mixture into a water/polar solvent phase and a non-polar solvent phase having a high oil-soluble active fraction dissolved and a substantially oil-insoluble active fraction precipitated; and recovering the non-polar solvent phase as a preservative.

* * * * *